US008933329B2

(12) United States Patent
Maeda et al.

(10) Patent No.: US 8,933,329 B2
(45) Date of Patent: Jan. 13, 2015

(54) MALEIMIDE-BASED COMPOUND, AND TAUTOMER OR STEREOISOMER THEREOF, DYE FOR PHOTOELECTRIC CONVERSION, AND SEMICONDUCTOR ELECTRODE, PHOTOELECTRIC CONVERSION ELEMENT AND PHOTOELECTROCHEMICAL CELL USING THE SAME

(75) Inventors: Katsumi Maeda, Tokyo (JP); Shin Nakamura, Tokyo (JP); Kentaro Nakahara, Tokyo (JP)

(73) Assignee: NEC Corporation, Tokyo (JP)

( * ) Notice: Subject to any disclaimer, the term of this patent is extended or adjusted under 35 U.S.C. 154(b) by 240 days.

(21) Appl. No.: 13/697,974

(22) PCT Filed: May 16, 2011

(86) PCT No.: PCT/JP2011/002706
§ 371 (c)(1),
(2), (4) Date: Nov. 14, 2012

(87) PCT Pub. No.: WO2011/145321
PCT Pub. Date: Nov. 24, 2011

(65) Prior Publication Data
US 2013/0056690 A1  Mar. 7, 2013

(30) Foreign Application Priority Data
May 18, 2010  (JP) ................................. 2010-114568

(51) Int. Cl.
H01L 51/00 (2006.01)
C07D 409/04 (2006.01)
C07D 495/04 (2006.01)
C09B 57/00 (2006.01)
H01G 9/20 (2006.01)

(52) U.S. Cl.
CPC ............ *C07D 409/04* (2013.01); *C07D 495/04* (2013.01); *C09B 57/008* (2013.01); *H01G 9/2059* (2013.01); *H01L 51/0059* (2013.01); *H01G 9/2031* (2013.01); *Y02E 10/542* (2013.01)
USPC ............ 136/263; 548/404; 548/541; 548/565

(58) Field of Classification Search
USPC ............................ 136/263; 548/404, 541, 565
See application file for complete search history.

(56) References Cited

U.S. PATENT DOCUMENTS

| 5,175,069 A | 12/1992 | Shuttleworth et al. |
| 5,179,207 A | 1/1993 | Krutak et al. |
| 6,369,124 B1 * | 4/2002 | Hoyle et al. .................... 522/63 |
| 7,250,521 B2 * | 7/2007 | Kraatz et al. .................. 548/565 |

FOREIGN PATENT DOCUMENTS

| JP | 5-188217 A | 7/1993 |
| JP | 9-255883 A | 9/1997 |
| JP | 2664194 B2 | 10/1997 |
| JP | 11-238905 A | 8/1999 |
| JP | 2001-76773 A | 3/2001 |
| JP | 2002-264502 A | 9/2002 |
| JP | 2004-95450 A | 3/2004 |
| JP | 2005-19124 A | 1/2005 |
| JP | 2005-19252 A | 1/2005 |

OTHER PUBLICATIONS

Brian O'Regan, et al., "A low-cost, high-efficiency solar cell based on dye-sensitized colloidal TiO2 films", Nature, Oct. 24, 1991, p. 737-740, vol. 353.

* cited by examiner

*Primary Examiner* — Gregory R Delcotto
(74) *Attorney, Agent, or Firm* — Sughrue Mion, PLLC

(57) ABSTRACT

It is an object to provide a maleimide-based compound having excellent photoelectric conversion characteristics, and a tautomer or a stereoisomer thereof, a dye for photoelectric conversion, a semiconductor electrode, a photoelectric conversion element, and a photoelectrochemical cell. In order to accomplish the above-described objects, a dye for photoelectric conversion including at least one compound represented by the following general formula (1) is provided.

[Chem. 1]

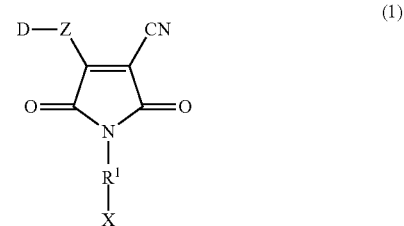

(In the formula (1), $R^1$ represents a direct bond, or a substituted or unsubstituted alkylene group. X represents an acidic group. D represents an organic group containing an electron-donating substituent. Z represents a linking group that has at least one hydrocarbon group selected from aromatic rings or heterocyclic rings).

9 Claims, 1 Drawing Sheet

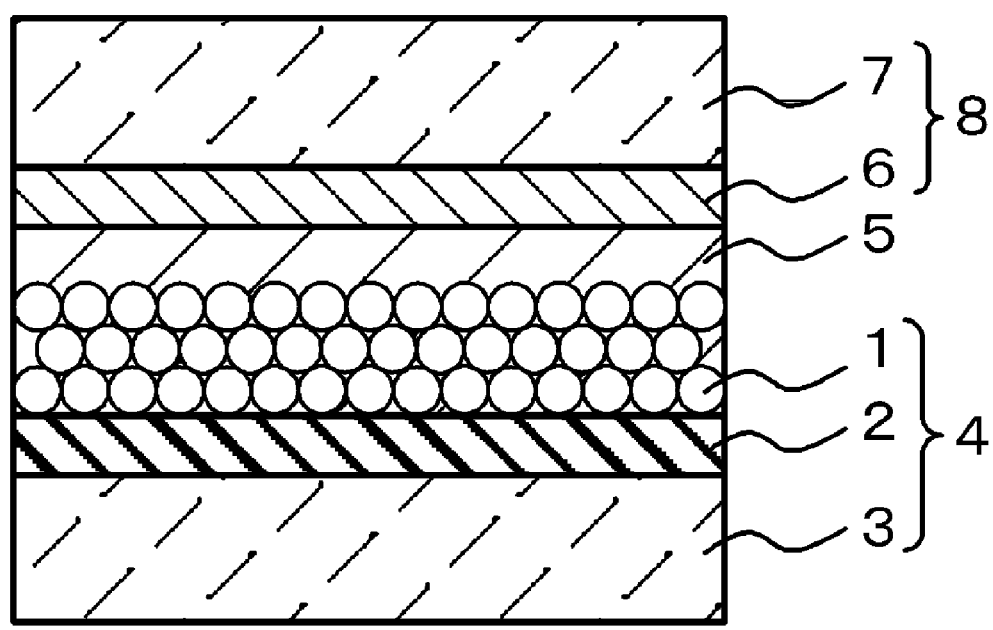

MALEIMIDE-BASED COMPOUND, AND TAUTOMER OR STEREOISOMER THEREOF, DYE FOR PHOTOELECTRIC CONVERSION, AND SEMICONDUCTOR ELECTRODE, PHOTOELECTRIC CONVERSION ELEMENT AND PHOTOELECTROCHEMICAL CELL USING THE SAME

CROSS REFERENCE TO RELATED APPLICATIONS

This application is a National Stage of International Application No. PCT/JP2011/002706, filed on May 16, 2011, which claims priority from Japanese Patent Application No. 2010-114568, filed on May 18, 2010, the contents of all of which are incorporated herein by reference in their entirety.

TECHNICAL FIELD

The present invention relates to a maleimide-based compound and a tautomer or a stereoisomer thereof, a dye for photoelectric conversion, and a semiconductor electrode, a photoelectric conversion element, and a photoelectrochemical cell using the same.

BACKGROUND ART

As a large amount of fossil fuels, such as petroleum, have been used hitherto, the accompanying increase in the concentration of $CO_2$ has given rise to global warming as a serious problem, and further, there has been a concern of depletion of the fossil fuels. Therefore, it has become a very important global issue as to how to meet the large amount of energy demand in the future. Under these circumstances, it has been studied actively to use clean solar light, which is infinite and does not generate harmful materials like nuclear power generation, for power generation. As a solar cell that converts light energy into electrical energy, inorganic solar cells such as a crystal silicon-based solar cell, a polycrystalline silicon-based solar cell, and an amorphous silicon-solar cell; and organic solar cells using an organic dye or a conductive polymer material, have been proposed.

Under these circumstances, a dye-sensitized solar cell (Graetzel type solar cell) (Non-Patent Document 1 and Patent Document 1) suggested by Graetzel et al., Switzerland, 1991, is anticipated as a next-generation solar cell since it is capable of providing a conversion efficiency at the same level as amorphous silicon using a simple and easy preparation process. The Graetzel type dye-sensitized solar cell includes a semiconductor electrode in which a semiconductor layer having a dye adsorbed thereon is formed on a conductive substrate; a counter electrode opposed to the electrode and formed of a conductive substrate; and an electrolyte layer held between both electrodes.

In this cell, the adsorbed dye absorbs light and then enters an excited state, and the electrons are injected into the semiconductor layer from the excited dye. The dye that had been in an oxidized state due to the discharge of the electrons returns to the original dye when the electrons move to the dye by an oxidation reaction of a redox agent in the electrolyte layer. Further, the redox agent which donates electrons to the dye is reduced again in the counter electrode. By such a series of the reactions, the function of a cell is realized.

In the Graetzel type dye-sensitized solar cell, the effective reaction surface area may be increased by about 1000 times by using porous titanium oxide formed by sintering fine particles in the semiconductor layer, thereby extracting a larger photocurrent than solar cells of the related art. In the Graetzel type dye-sensitized solar cell, a ruthenium complex is used as a sensitive dye, and specifically, a bipyridine complex of ruthenium, such as a cis-bis(isothiocyanato)-bis-(2,2'-bipyridine-4,4'-dicarboxylic acid) ruthenium (II) bi-tetrabutylammonium complex, cis-bis(isothiocyanato)-bis-(2,2'-bipyridine-4,4'-dicarboxylic acid) ruthenium (II), or a terpyridine complex of ruthenium, such as tris(isothiocyanato) (2,2':6', 2"-terpyridyl 4,4',4"-tricarboxylic acid) ruthenium (II) tri-tetrabutylammonium complex, is used.

Further, in Patent Document 6, a novel merocyanine dye and a preparation method therefor are described. Further, in Patent Document 7, a semiconductor for a photoelectric conversion material, which includes a predetermined heterocyclic compound, is described.

RELATED DOCUMENT

Patent Document

[Patent Document 1] Japanese Patent No. 2664194
[Patent Document 2] Japanese Laid-open Patent Publication No. 2004-95450
[Patent Document 3] Japanese Laid-open Patent Publication No. 2001-76773
[Patent Document 4] Japanese Laid-open Patent Publication No. 11-238905
[Patent Document 5] Japanese Laid-open Patent Publication No. 2005-19252
[Patent Document 6] Japanese Laid-open Patent Publication No. 9-255883
[Patent Document 7] Japanese Laid-open Patent Publication No. 2005-19124
[Non-Patent Document 1] Brian O'Regan, Michael Graetzel, "A low-cost, high-efficiency solar cell based on dye-sensitized colloidal $TiO_2$ films", Nature, British, Nature Publishing Group, Oct. 24, 1991, Vol. 353, p. 737-740

DISCLOSURE OF THE INVENTION

As a problem of a dye-sensitized solar cell using a ruthenium complex, use of ruthenium that is a noble metal in raw materials for the dye may be mentioned. When the ruthenium complex is used for mass production of a dye-sensitized solar cell, a problem of resource constraint occurs, and the solar cell becomes expensive, thereby interfering with the distribution of the cells.

In this regard, a number of organic dyes of non-ruthenium complexes have recently been proposed as a sensitizing dye in dye-sensitized solar cells. Examples thereof include a coumarin-based dye (Patent Document 2), a cyanine-based dye (Patent Document 3), and a merocyanine-based dye (Patent Documents 4 and 5). These organic dyes have a higher molar absorption coefficient and a greater degree of freedom of molecular design than ruthenium complexes, and accordingly, it is expected to develop a dye having a high photoelectric conversion efficiency. However, these organic dyes have a problem that it is difficult to obtain a higher photoelectric conversion efficiency in comparison to the ruthenium complexes.

The present invention has been made to solve the above-described problems and an object thereof is to provide a maleimide-based compound having excellent photoelectric conversion characteristics, and a tautomer or a stereoisomer thereof, a dye for photoelectric conversion, and a semiconductor electrode, a photoelectric conversion element, and photoelectrochemical cell.

The compound of the present invention is a maleimide-based compound represented by the following general formula (1), and a tautomer or a stereoisomer thereof.

[Chem. 1]

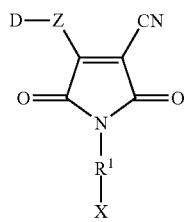

(1)

(In the formula (1), $R^1$ represents a direct bond, or a substituted or unsubstituted alkylene group. X represents an acidic group. D represents an organic group containing an electron-donating substituent. Z represents a linking group that has at least one hydrocarbon group selected from aromatic rings or heterocyclic rings.)

The dye for photoelectric conversion of the present invention may include at least one kind of maleimide-based compound and a tautomer or a stereoisomer thereof of the present invention.

The semiconductor electrode for a photoelectrochemical cell of the present invention may include a semiconductor layer containing the dye for photoelectric conversion of the present invention.

The photoelectric conversion element for a photoelectrochemical cell of the present invention may include the semiconductor electrode for a photoelectrochemical cell of the present invention.

In addition, the photoelectrochemical cell of the present invention may include the photoelectric conversion element for a photoelectrochemical cell of the present invention.

According to the present invention, a maleimide-based compound having excellent photoelectric conversion characteristics, and a tautomer or a stereoisomer thereof, a dye for photoelectric conversion, a semiconductor electrode, a photoelectric conversion element, and a photoelectrochemical cell are achieved.

BRIEF DESCRIPTION OF THE DRAWINGS

The above and other objects, advantages, and features of the present invention will be more apparent from the following description of certain preferred embodiments taken in conjunction with the accompanying drawings, in which FIG. 1 is a cross-sectional view schematically illustrating a constitution of an example of the photoelectric conversion element of the present embodiment.

DESCRIPTION OF EMBODIMENTS

Hereinbelow, the embodiments of the present invention will be described in detail.

<Maleimide-Based Compound, and Tautomer or Stereomer thereof>

The compound of the present embodiment is a maleimide-based compound represented by the following general formula (1), and a tautomer or a stereoisomer thereof.

[Chem. 2]

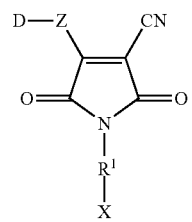

(1)

In the formula (1), $R^1$ represents a direct bond, or a substituted or unsubstituted alkylene group (for example, a methylene group, an ethylene group, a propylene group, and a butylene group, and among these, an alkylene group having 2 or less carbon atoms is preferred).

X represents an acidic group (for example, a carboxyl group, a hydroxyl group, a sulfonic acid group, or a phosphonic acid group, and among these, a carboxyl group is particularly preferred). The maleimide-based compound represented by the general formula (1) is used after being adsorbed on a semiconductor layer in the preparation of a semiconductor electrode. Accordingly, it is necessary that a functional group capable of being adsorbed on a semiconductor layer be included in the molecule. In the maleimide-based compound of the present embodiment, an acidic group represented by X serves as such a functional group.

Furthermore, D represents an organic group containing an electron-donating substituent. Examples of the organic group D containing an electron-donating substituent include, but not limited to, organic groups represented by the formula (2) or (3) and organic groups represented by the chemical formulas (D1) to (D9).

[Chem. 3]

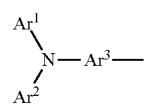

(2)

[Chem. 4]

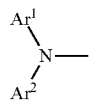

(3)

$Ar^1$ and $Ar^2$ in the formula (2) each independently represent a substituted or unsubstituted alkyl group, a substituted or unsubstituted aryl group, or a heterocyclic group. Examples of the substituted or unsubstituted alkyl group include alkyl groups having 1 to 8 carbon atoms, such as a methyl group, an ethyl group, a propyl group, an n-butyl group, a pentyl group, a hexyl group, a heptyl group, and an octyl group, and aralkyl groups such as a benzyl group; examples of the substituent bonded to the alkyl group include a hydroxyl group, alkoxy groups (for example, alkoxy groups having 1 to 4 carbon atoms), and a phenyl group. Examples of the substituted or unsubstituted aryl group include substituted or unsubstituted aryl groups having 6 to 22 carbon atoms, such as a phenyl group, a tolyl group, a 4-t-butylphenyl group, a 3,5-di-t-butylphenyl group, a 4-methoxyphenyl group, a 4-hexyloxyphenyl group, a 4-octyloxyphenyl group, a 4-(N,N-dimethylamino)phenyl group, and a 4-(N,N-diphenylamino)phenyl group; and examples of the substituent bonded to the aryl group include alkyl groups (for example, alkyl groups having 1 to 8 carbon atoms), a hydroxyl group, alkoxy groups (for example, alkoxy groups having 1 to 8 carbon atoms), N,N-dialkylamino groups (in which the alkyl group moiety is, for example, an alkyl group having 1 to 8 carbon atoms), and N,N-diphenylamino groups. Examples of the substituted or unsubstituted heterocyclic group include a thienyl group, a furyl group, a pyrrolyl group, an indolyl group, and a carbazolyl group, and examples of the substituent bonded to the heterocyclic group include alkyl groups (for example, alkyl groups having 1 to 8 carbon atoms), a hydroxyl group, and alkoxy groups (for example, alkoxy groups having 1 to 8 carbon atoms). Further, $Ar^3$ represents a substituted or unsubstituted arylene group, or a substituted or unsubstituted divalent heterocyclic group. Examples of the substituted or unsubstituted arylene group include a phenylene group and a naphthylene group; and examples of the substituent bonded to the arylene group include alkyl groups (for example, alkyl groups having 1 to 8 carbon atoms), a hydroxyl group, and alkoxy groups (for example, alkoxy groups having 1 to 8 carbon atoms). Examples of the substituted or unsubstituted divalent heterocyclic group include a thiophenediyl group, a furandiyl group, and a pyrrolediyl group; and examples of the substituent bonded to the divalent heterocyclic ring include alkyl groups (for example, alkyl groups having 1 to 8 carbon atoms), a hydroxyl group, and alkoxy groups (for example, alkoxy groups having 1 to 8 carbon atoms).

[Chem. 5]

(D1)
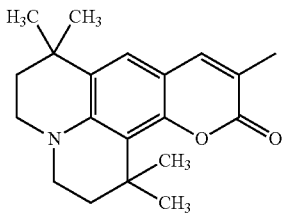

(D2)
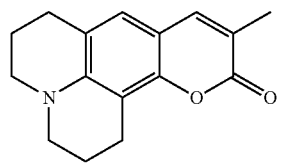

(D3)
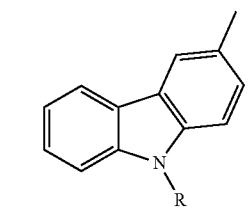

(D4)
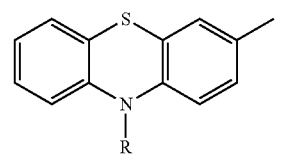

(D5)
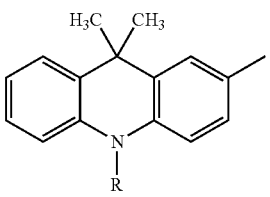

(D6)
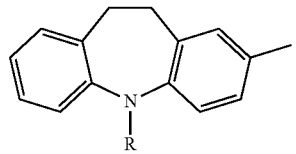

(D7)
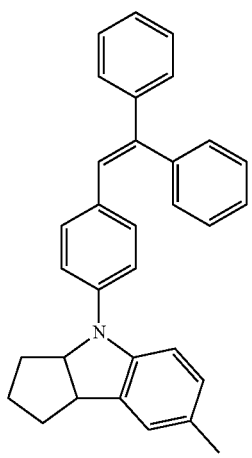

(D8)
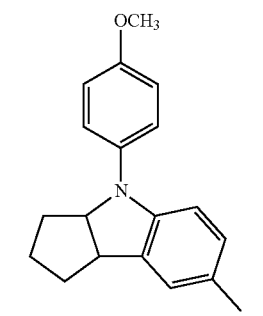

(D9)
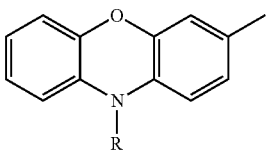

Further, R in the formulas (D1) to (D9) represents a substituted or unsubstituted alkyl group (for example, alkyl groups having 1 to 8 carbon atoms, such as a methyl group, an ethyl group, a propyl group, an n-butyl group, an isobutyl group, a pentyl group, a hexyl group, a heptyl group, and an octyl group), or a substituted or unsubstituted aryl group (for example, a phenyl group, a tolyl group, a 4-t-butylphenyl group, a 3,5-di-t-butylphenyl group, a 4-methoxyphenyl group, and a 4-(N,N-dimethyl)aminophenyl group).

Z in the general formula (1) represents a linking group that has at least one hydrocarbon group selected from aromatic rings or heterocyclic rings. The linking group Z is not particularly limited, however, is preferably an atomic moiety capable of conjugating with a maleimide ring bonded to Z (that is, a maleimide ring represented in the general formula (1)). Further, the linking group Z is preferably a linking group having at least a structure represented by the following general formula (4).

[Chem. 6]

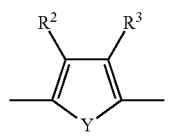

(4)

In the general formula (4), $R^2$ and $R^3$ each independently represent a hydrogen atom, a substituted or unsubstituted, linear or branched alkyl group, or a substituted or unsubstituted, linear or branched alkoxy group, or $R^2$ and $R^3$ may be bonded to each other to form a ring. Examples of the substituted or unsubstituted alkyl group include alkyl groups having 1 to 8 carbon atoms, such as a methyl group, an ethyl group, a propyl group, an n-butyl group, a pentyl group, a hexyl group, a heptyl group, and an octyl group, and examples of the substituent bonded to the alkyl group include a hydroxyl group and an alkoxy group. Examples of the alkoxy group include alkoxy groups having 1 to 4 carbon atoms, such as a methoxy group, an ethoxy group, a propoxy group, and a butoxyl group.

In the general formula (4), Y represents an oxygen atom, a sulfur atom, or NRa; and Ra represents a hydrogen atom, a substituted or unsubstituted, linear or branched alkyl group, or a substituted or unsubstituted aryl group. Examples of the substituted or unsubstituted alkyl group include alkyl group having 1 to 8 carbon atoms, such as a methyl group, an ethyl group, a propyl group, an n-butyl group, a pentyl group, a hexyl group, a heptyl group, and an octyl group, and aralkyl groups such as a benzyl group; and examples of the substituent bonded to the alkyl group include a hydroxyl group, an alkoxy group, and a phenyl group. Examples of the substituted or unsubstituted aryl group include a phenyl group, a tolyl group, a 4-t-butylphenyl group, a 3,5-di-t-butylphenyl group, a 4-methoxyphenyl group, and a 4-(N,N-dimethylamino)phenyl group. Examples of the substituent bonded to the aryl group include an alkyl group, a hydroxyl group, an alkoxy group, and an N,N-dialkylamino group.

Specific examples of the linking group Z are shown below by the formulas (Z1) to (Z28), however are not limited thereto. When plural heterocyclic and aromatic rings are present, the carbon atoms constituting the ring may be directly bonded to each other, or may form a condensed ring and be bonded to each other. Further, the linking groups may be groups formed by linking the plural linking groups.

[Chem. 7]

(Z1)

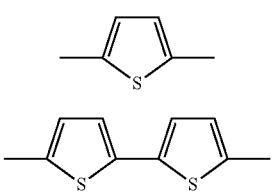

(Z2)

[Chem. 8]

(Z3)
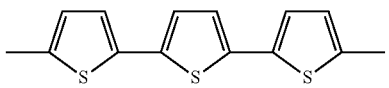

(Z4)
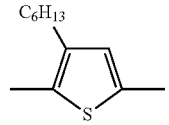

(Z5)
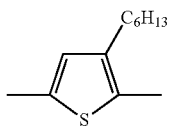

(Z6)
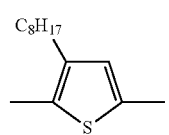

(Z7)
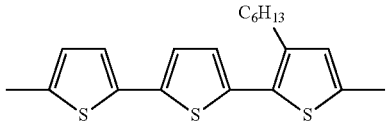

(Z8)
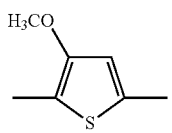

(Z9)
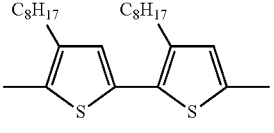

(Z10)
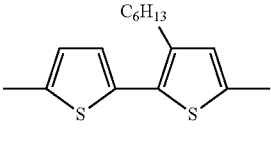

(Z11)
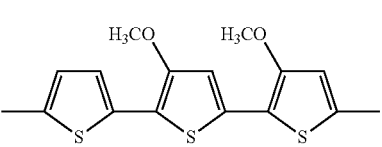

(Z12)
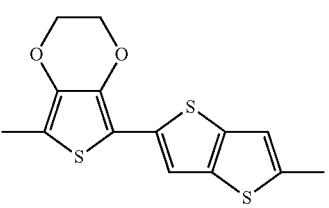

(Z13)
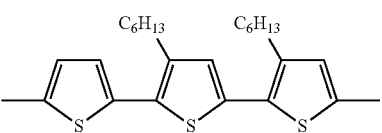

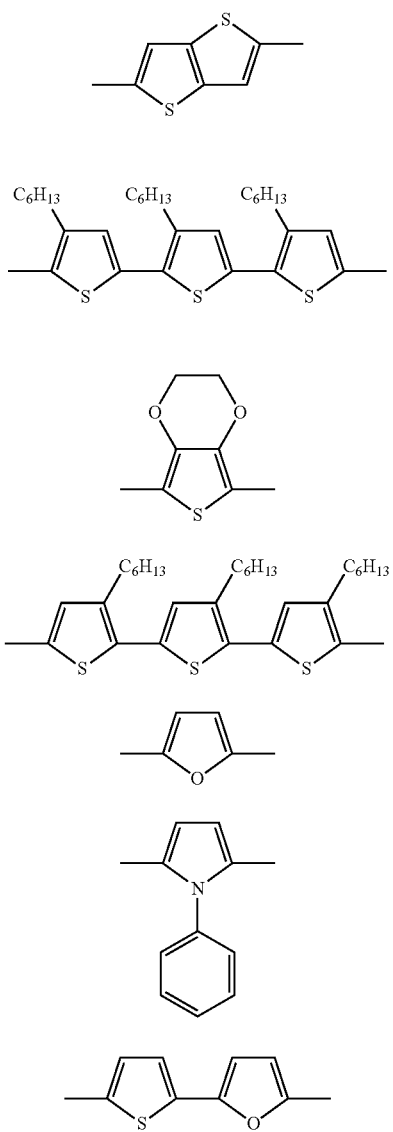
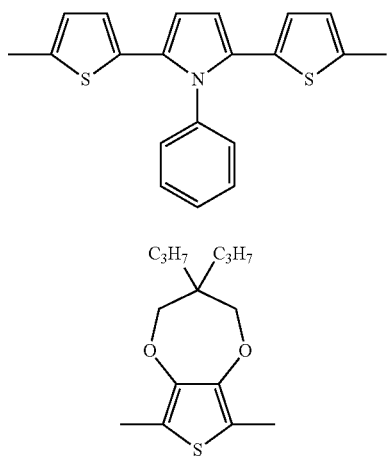
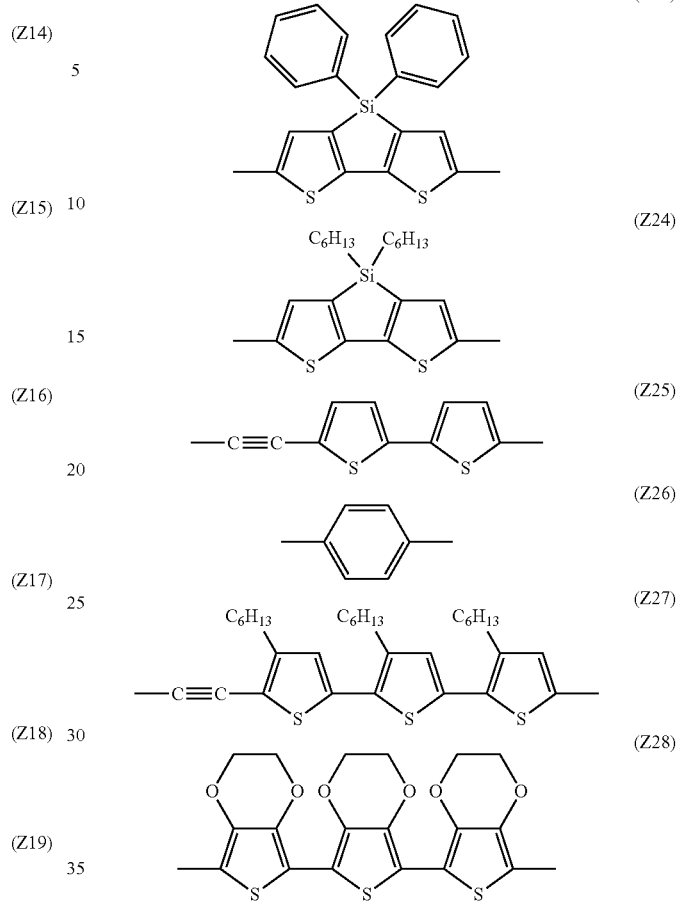

Furthermore, examples of the combination of D and Z in the maleimide-based compound represented by the general formula (1), or a tautomer or a stereoisomer thereof include (a to i)-(1 to 27) below.

TABLE 1

| | D | Z |
|---|---|---|
| a-1 | Formula (2) | Z1 |
| a-2 | Formula (2) | Z2 |
| a-3 | Formula (2) | Z3 |
| a-4 | Formula (2) | Z4 |
| a-5 | Formula (2) | Z5 |
| a-6 | Formula (2) | Z6 |
| a-7 | Formula (2) | Z7 |
| a-8 | Formula (2) | Z8 |
| a-9 | Formula (2) | Z9 |
| a-10 | Formula (2) | Z10 |
| a-11 | Formula (2) | Z11 |
| a-12 | Formula (2) | Z12 |
| a-13 | Formula (2) | Z13 |
| a-14 | Formula (2) | Z14 |
| a-15 | Formula (2) | Z15 |
| a-16 | Formula (2) | Z16 |
| a-17 | Formula (2) | Z17 |
| a-18 | Formula (2) | Z18 |
| a-19 | Formula (2) | Z19 |
| a-20 | Formula (2) | Z20 |
| a-21 | Formula (2) | Z21 |
| a-22 | Formula (2) | Z22 |
| a-23 | Formula (2) | Z23 |
| a-24 | Formula (2) | Z24 |
| a-25 | Formula (2) | Z25 |

TABLE 1-continued

|  | D | Z |
|---|---|---|
| a-26 | Formula (2) | Z26 |
| a-27 | Formula (2) | Z27 |
| a-28 | Formula (2) | Z28 |
| b-1 | Formula (3) | Z1 |
| b-2 | Formula (3) | Z2 |
| b-3 | Formula (3) | Z3 |
| b-4 | Formula (3) | Z4 |
| b-5 | Formula (3) | Z5 |
| b-6 | Formula (3) | Z6 |
| b-7 | Formula (3) | Z7 |
| b-8 | Formula (3) | Z8 |
| b-9 | Formula (3) | Z9 |
| b-10 | Formula (3) | Z10 |
| b-11 | Formula (3) | Z11 |
| b-12 | Formula (3) | Z12 |
| b-13 | Formula (3) | Z13 |
| b-14 | Formula (3) | Z14 |
| b-15 | Formula (3) | Z15 |
| b-16 | Formula (3) | Z16 |
| b-17 | Formula (3) | Z17 |
| b-18 | Formula (3) | Z18 |
| b-19 | Formula (3) | Z19 |
| b-20 | Formula (3) | Z20 |
| b-21 | Formula (3) | Z21 |
| b-22 | Formula (3) | Z22 |
| b-23 | Formula (3) | Z23 |
| b-24 | Formula (3) | Z24 |
| b-25 | Formula (3) | Z25 |
| b-26 | Formula (3) | Z26 |
| b-27 | Formula (3) | Z27 |
| b-28 | Formula (3) | Z28 |
| c-1 | D1 | Z1 |
| c-2 | D1 | Z2 |
| c-3 | D1 | Z3 |
| c-4 | D1 | Z4 |
| c-5 | D1 | Z5 |
| c-6 | D1 | Z6 |
| c-7 | D1 | Z7 |
| c-8 | D1 | Z8 |
| c-9 | D1 | Z9 |
| c-10 | D1 | Z10 |
| c-11 | D1 | Z11 |
| c-12 | D1 | Z12 |
| c-13 | D1 | Z13 |
| c-14 | D1 | Z14 |
| c-15 | D1 | Z15 |
| c-16 | D1 | Z16 |
| c-17 | D1 | Z17 |
| c-18 | D1 | Z18 |
| c-19 | D1 | Z19 |
| c-20 | D1 | Z20 |
| c-21 | D1 | Z21 |
| c-22 | D1 | Z22 |
| c-23 | D1 | Z23 |
| c-24 | D1 | Z24 |
| c-25 | D1 | Z25 |
| c-26 | D1 | Z26 |
| c-27 | D1 | Z27 |
| c-28 | D1 | Z28 |

TABLE 2

|  | D | Z |
|---|---|---|
| d-1 | D2 | Z1 |
| d-2 | D2 | Z2 |
| d-3 | D2 | Z3 |
| d-4 | D2 | Z4 |
| d-5 | D2 | Z5 |
| d-6 | D2 | Z6 |
| d-7 | D2 | Z7 |
| d-8 | D2 | Z8 |
| d-9 | D2 | Z9 |
| d-10 | D2 | Z10 |
| d-11 | D2 | Z11 |
| d-12 | D2 | Z12 |
| d-13 | D2 | Z13 |
| d-14 | D2 | Z14 |
| d-15 | D2 | Z15 |
| d-16 | D2 | Z16 |
| d-17 | D2 | Z17 |
| d-18 | D2 | Z18 |
| d-19 | D2 | Z19 |
| d-20 | D2 | Z20 |
| d-21 | D2 | Z21 |
| d-22 | D2 | Z22 |
| d-23 | D2 | Z23 |
| d-24 | D2 | Z24 |
| d-25 | D2 | Z25 |
| d-26 | D2 | Z26 |
| d-27 | D2 | Z27 |
| d-28 | D2 | Z28 |
| e-1 | D3 | Z1 |
| e-2 | D3 | Z2 |
| e-3 | D3 | Z3 |
| e-4 | D3 | Z4 |
| e-5 | D3 | Z5 |
| e-6 | D3 | Z6 |
| e-7 | D3 | Z7 |
| e-8 | D3 | Z8 |
| e-9 | D3 | Z9 |
| e-10 | D3 | Z10 |
| e-11 | D3 | Z11 |
| e-12 | D3 | Z12 |
| e-13 | D3 | Z13 |
| e-14 | D3 | Z14 |
| e-15 | D3 | Z15 |
| e-16 | D3 | Z16 |
| e-17 | D3 | Z17 |
| e-18 | D3 | Z18 |
| e-19 | D3 | Z19 |
| e-20 | D3 | Z20 |
| e-21 | D3 | Z21 |
| e-22 | D3 | Z22 |
| e-23 | D3 | Z23 |
| e-24 | D3 | Z24 |
| e-25 | D3 | Z25 |
| e-26 | D3 | Z26 |
| e-27 | D3 | Z27 |
| e-28 | D3 | Z28 |
| f-1 | D4 | Z1 |
| f-2 | D4 | Z2 |
| f-3 | D4 | Z3 |
| f-4 | D4 | Z4 |
| f-5 | D4 | Z5 |
| f-6 | D4 | Z6 |
| f-7 | D4 | Z7 |
| f-8 | D4 | Z8 |
| f-9 | D4 | Z9 |
| f-10 | D4 | Z10 |
| f-11 | D4 | Z11 |
| f-12 | D4 | Z12 |
| f-13 | D4 | Z13 |
| f-14 | D4 | Z14 |
| f-15 | D4 | Z15 |
| f-16 | D4 | Z16 |
| f-17 | D4 | Z17 |
| f-18 | D4 | Z18 |
| f-19 | D4 | Z19 |
| f-20 | D4 | Z20 |
| f-21 | D4 | Z21 |
| f-22 | D4 | Z22 |
| f-23 | D4 | Z23 |
| f-24 | D4 | Z24 |
| f-25 | D4 | Z25 |
| f-26 | D4 | Z26 |
| f-27 | D4 | Z27 |
| f-28 | D4 | Z28 |

TABLE 3

| | D | Z |
|---|---|---|
| g-1 | D5 | Z1 |
| g-2 | D5 | Z2 |
| g-3 | D5 | Z3 |
| g-4 | D5 | Z4 |
| g-5 | D5 | Z5 |
| g-6 | D5 | Z6 |
| g-7 | D5 | Z7 |
| g-8 | D5 | Z8 |
| g-9 | D5 | Z9 |
| g-10 | D5 | Z10 |
| g-11 | D5 | Z11 |
| g-12 | D5 | Z12 |
| g-13 | D5 | Z13 |
| g-14 | D5 | Z14 |
| g-15 | D5 | Z15 |
| g-16 | D5 | Z16 |
| g-17 | D5 | Z17 |
| g-18 | D5 | Z18 |
| g-19 | D5 | Z19 |
| g-20 | D5 | Z20 |
| g-21 | D5 | Z21 |
| g-22 | D5 | Z22 |
| g-23 | D5 | Z23 |
| g-24 | D5 | Z24 |
| g-25 | D5 | Z25 |
| g-26 | D5 | Z26 |
| g-27 | D5 | Z27 |
| g-28 | D5 | Z28 |
| h-1 | D6 | Z1 |
| h-2 | D6 | Z2 |
| h-3 | D6 | Z3 |
| h-4 | D6 | Z4 |
| h-5 | D6 | Z5 |
| h-6 | D6 | Z6 |
| h-7 | D6 | Z7 |
| h-8 | D6 | Z8 |
| h-9 | D6 | Z9 |
| h-10 | D6 | Z10 |
| h-11 | D6 | Z11 |
| h-12 | D6 | Z12 |
| h-13 | D6 | Z13 |
| h-14 | D6 | Z14 |
| h-15 | D6 | Z15 |
| h-16 | D6 | Z16 |
| h-17 | D6 | Z17 |
| h-18 | D6 | Z18 |
| h-19 | D6 | Z19 |
| h-20 | D6 | Z20 |
| h-21 | D6 | Z21 |
| h-22 | D6 | Z22 |
| h-23 | D6 | Z23 |
| h-24 | D6 | Z24 |
| h-25 | D6 | Z25 |
| h-26 | D6 | Z26 |
| h-27 | D6 | Z27 |
| h-28 | D6 | Z28 |
| i-1 | D7 | Z1 |
| i-2 | D7 | Z2 |
| i-3 | D7 | Z3 |
| i-4 | D7 | Z4 |
| i-5 | D7 | Z5 |
| i-6 | D7 | Z6 |
| i-7 | D7 | Z7 |
| i-8 | D7 | Z8 |
| i-9 | D7 | Z9 |
| i-10 | D7 | Z10 |
| i-11 | D7 | Z11 |
| i-12 | D7 | Z12 |
| i-13 | D7 | Z13 |
| i-14 | D7 | Z14 |
| i-15 | D7 | Z15 |
| i-16 | D7 | Z16 |
| i-17 | D7 | Z17 |
| i-18 | D7 | Z18 |
| i-19 | D7 | Z19 |
| i-20 | D7 | Z20 |
| i-21 | D7 | Z21 |
| i-22 | D7 | Z22 |
| i-23 | D7 | Z23 |
| i-24 | D7 | Z24 |
| i-25 | D7 | Z25 |
| i-26 | D7 | Z26 |
| i-27 | D7 | Z27 |
| i-28 | D7 | Z28 |

TABLE 4

| | D | Z |
|---|---|---|
| j-1 | D8 | Z1 |
| j-2 | D8 | Z2 |
| j-3 | D8 | Z3 |
| j-4 | D8 | Z4 |
| j-5 | D8 | Z5 |
| j-6 | D8 | Z6 |
| j-7 | D8 | Z7 |
| j-8 | D8 | Z8 |
| j-9 | D8 | Z9 |
| j-10 | D8 | Z10 |
| j-11 | D8 | Z11 |
| j-12 | D8 | Z12 |
| j-13 | D8 | Z13 |
| j-14 | D8 | Z14 |
| j-15 | D8 | Z15 |
| j-16 | D8 | Z16 |
| j-17 | D8 | Z17 |
| j-18 | D8 | Z18 |
| j-19 | D8 | Z19 |
| j-20 | D8 | Z20 |
| j-21 | D8 | Z21 |
| j-22 | D8 | Z22 |
| j-23 | D8 | Z23 |
| j-24 | D8 | Z24 |
| j-25 | D8 | Z25 |
| j-26 | D8 | Z26 |
| j-27 | D8 | Z27 |
| j-28 | D8 | Z28 |
| k-1 | D9 | Z1 |
| k-2 | D9 | Z2 |
| k-3 | D9 | Z3 |
| k-4 | D9 | Z4 |
| k-5 | D9 | Z5 |
| k-6 | D9 | Z6 |
| k-7 | D9 | Z7 |
| k-8 | D9 | Z8 |
| k-9 | D9 | Z9 |
| k-10 | D9 | Z10 |
| k-11 | D9 | Z11 |
| k-12 | D9 | Z12 |
| k-13 | D9 | Z13 |
| k-14 | D9 | Z14 |
| k-15 | D9 | Z15 |
| k-16 | D9 | Z16 |
| k-17 | D9 | Z17 |
| k-18 | D9 | Z18 |
| k-19 | D9 | Z19 |
| k-20 | D9 | Z20 |
| k-21 | D9 | Z21 |
| k-22 | D9 | Z22 |
| k-23 | D9 | Z23 |
| k-24 | D9 | Z24 |
| k-25 | D9 | Z25 |
| k-26 | D9 | Z26 |
| k-27 | D9 | Z27 |
| k-28 | D9 | Z28 |

Furthermore, examples of the specific structure other than Z and D of the maleimide-based compound represented by the general formula (1) are shown below.

[Chem. 10]

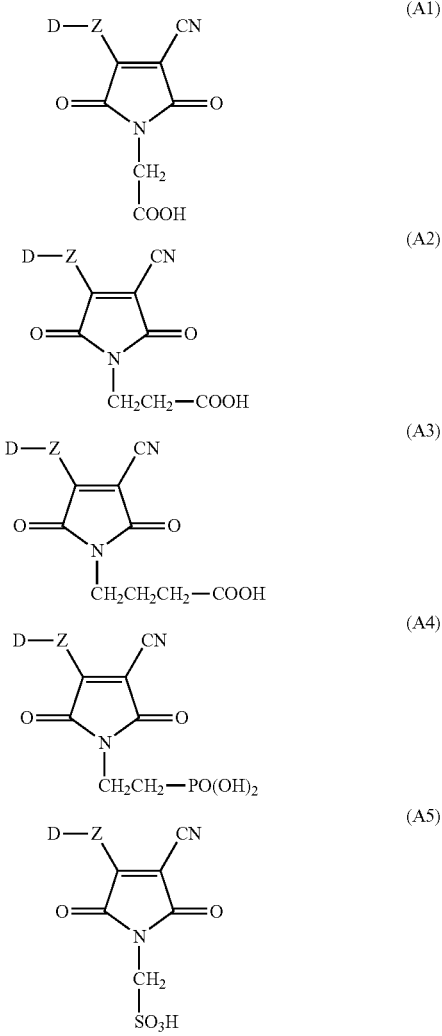

<Photoelectric Conversion Element>

FIG. 1 shows a cross-sectional view schematically illustrating an example of the configuration of the photoelectric conversion element of the present embodiment. The photoelectric conversion element shown in FIG. 1 includes a semiconductor electrode 4, a counter electrode 8, and an electrolyte layer 5 held between the two electrodes. The semiconductor electrode 4 includes a light-transmissive substrate 3, a transparent conductive layer 2, and a semiconductor layer 1. The counter electrode 8 includes a catalyst layer 6 and a substrate 7. Further, the semiconductor layer 1 has a dye adsorbed thereon.

When light is incident on the photoelectric conversion element of the present embodiment, the dye adsorbed on the semiconductor layer 1 is excited, thereby emitting electrons. The electrons move to the conduction band of the semiconductor, and further move to a transparent conductive layer 2 by diffusion. The electrons in the transparent conductive layer 2 move to a counter electrode 8 via an external circuit (not shown). Then, the photoelectric conversion element is configured such that the electrons return to the dye in an oxidized state via an electrolyte layer 5, and thus the dye is regenerated and serves as a cell. Hereinafter, the respective constituent elements will be described using FIG. 1.

<Semiconductor Electrode>

The semiconductor electrode 4 includes the light-transmissive substrate 3, the transparent conductive layer 2, and the semiconductor layer 1. FIG. 1 shows a structure where the light-transmissive substrate 3, the transparent conductive layer 2, and the semiconductor layer 1 are laminated in this order from the outside toward the inside of the element. Further, the dye (not described in FIG. 1) is adsorbed on the semiconductor layer 1.

<Conductive Substrate>

The conductive substrate may have a monolayer structure where the substrate itself has conductivity, or may have a bilayer structure where a conductive layer is formed on a substrate. FIG. 1 shows an example of the conductive substrate having a bilayer structure where the transparent conductive layer 2 is formed on the light-transmissive substrate 3. Examples of the substrate include a glass substrate, a plastic substrate, and a metal plate, and among these, a substrate having high light transmissivity, for example, a transparent substrate, is particularly preferred. Examples of the material of the transparent plastic substrate include polyethylene terephthalate (PET), polyethylene naphthalate (PEN), polycarbonate (PC), polycycloolefin, and polyphenylene sulfide. In addition, the type of the conductive layer formed on the substrate (for example, the light-transmissive substrate 3) is not particularly limited, however, the transparent conductive layer 2 constituted by transparent materials such as, for example, Indium Tin Oxide (ITO), Fluorine-doped Tin Oxide (FTO), Indium Zinc Oxide (IZO), and tin oxide ($SnO_2$) is preferred. The transparent conductive layer 2 may be formed into a film on the entire or partial surface of the substrate. The film thickness of the transparent conductive layer 2 can be appropriately selected, however, the film thickness is preferably more than or equal to about 0.02 µm and less than or equal to 10 µm. The method for preparing the transparent conductive layer 2 can be achieved using well-known techniques, and therefore, description thereof is omitted here.

In addition, a metal lead wire can also be used in the conductive substrate of the present embodiment in order to reduce the resistance of the conductive substrate. Examples of the material of the metal lead wire include metals such as aluminum, copper, gold, silver, platinum, and nickel. A method in which a metal lead wire is prepared using vapor deposition, sputtering, or the like, and ITO or FTO is provided thereon, a method in which the transparent conductive layer 2 is provided on a substrate (for example, the light-transmissive substrate 3), and then a metal lead wire is prepared on the transparent conductive layer 2, or the like, may be applied.

Hereinafter, description will be made using an example of a conductive substrate having a bilayer structure where the transparent conductive layer 2 is formed on the light-transmissive substrate 3.

<Semiconductor Layer>

As the material constituting the semiconductor layer 1, elemental semiconductors such as silicon and germanium, or compounds having a chalcogenide of a metal or a perovskite structure, or the like can be used. Examples of the metal chalcogenide include oxides of titanium, tin, zinc, iron, tungsten, indium, zirconium, vanadium, niobium, tantalum, strontium, hafnium, cerium, lanthanum, or the like; sulfides of cadmium, zinc, lead, silver, antimony, bismuth, or the like; selenides of cadmium, lead, or the like; and tellurides of cadmium or the like. Examples of other compound semiconductor include phosphides of zinc, gallium, indium, cadmium, or the like, gallium arsenide, copper indium selenide, and copper indium sulfide. In addition, examples of the compound having a perovskite structure include known semiconductor materials, such as barium titanate, strontium titanate, and potassium niobate. These semiconductor materials can be used alone or in a mixture of two or more kinds thereof. Among these, from the viewpoint of conversion efficiency, stability, or safety, the semiconductor layer 1 is preferably constituted by semiconductor materials containing zinc oxide or titanium oxide, or most preferably constituted by semiconductor material containing titanium oxide. More specific examples of the titanium oxide include various titanium oxide or oxygen-containing titanium complexes, such as anatase type titanium oxide, rutile type titanium oxide, amorphous titanium oxide, metatitanic acid, and orthotitanic acid. Among these, from the viewpoint of further improving the stability of the photoelectric conversion, the anatase type titanium oxide is preferred.

Examples of the shape of the semiconductor layer 1 include a porous semiconductor layer obtained by sintering semiconductor fine particles or the like, and a semiconductor layer in the form of a thin film obtained by a sol-gel method, a sputtering method, a spray-pyrolysis method, or the like. Further, the semiconductor layer 1 may also be a fibrous semiconductor layer or a semiconductor layer including needle-shaped crystals. The shape of the semiconductor layer 1 can be appropriately selected according to the intended use of the photoelectric conversion element. Among these, from the viewpoint of the dye adsorption amount or the like, the semiconductor layer 1 is preferably one having a relatively large specific surface area, such as a porous semiconductor layer and a semiconductor layer including needle-shaped crystals. In addition, from the viewpoint that the utilization of the incident light, or the like can be adjusted with the particle diameter of semiconductor fine particles, it is preferable to use a porous semiconductor layer formed from the semiconductor fine particles as the semiconductor layer 1. Further, the semiconductor layer 1 may be a monolayer or a multilayer. By using multilayer, the semiconductor layer 1 having a sufficient thickness can be more easily formed. In addition, the porous multilayer semiconductor layer 1 formed from the semiconductor fine particles may be composed of plural semiconductor layers having different average particle diameters of the semiconductor fine particles. For example, the average particle diameter of the semiconductor fine particles of the semiconductor layer closer to the light incident side (first semiconductor layer) may be smaller than the semiconductor layer farther from the light incident side (second semiconductor layer). In this way, much light is absorbed in the first semiconductor layer, the light having passing through the first semiconductor layer is efficiently scattered into the second semiconductor layer and returned to first semiconductor layer, and the returned light is absorbed in the first semiconductor layer, thereby making it possible to further improve the overall light absorption rate. The film thickness of the semiconductor layer 1 is not particularly limited, however, from the viewpoint of transmission, conversion efficiency, or the like, it is, for example, more than or equal to 0.5 μm and less than or equal to 45 μm. The specific surface area of the semiconductor layer 1 can be, for example, more than or equal to 10 m$^2$/g and less than or equal to 200 m$^2$/g, from the viewpoint of absorbing a large amount of the dye.

Furthermore, in the constitution where the dye is adsorbed in the porous semiconductor layer 1, the porosity of the porous semiconductor layer 1 is preferably more than or equal to 40% and less than or equal to 80% in order to carry out the charge transport by more sufficiently diffusing the ions in the electrolyte. Further, the porosity is a proportion in percentage of the volume occupied by one pore in the semiconductor layer 1, relative to the volume of the semiconductor layer 1.

<Method of Forming Semiconductor Layer>

Next, a method for forming the semiconductor layer 1 will be described using the porous semiconductor layer 1. The porous semiconductor layer 1 is formed by adding semiconductor fine particles to a dispersion medium such as an organic solvent and water together with, for example, an organic compound such as a resin and a dispersing agent to give a suspension, and coating the suspension onto a conductive substrate (in FIG. 1, the transparent conductive layer 2), followed by drying and calcining. When the organic compound is added to the dispersion medium together with the semiconductor fine particles, the organic compound is burned at the time of calcining, and thus, it becomes possible to achieve sufficient gaps in the porous semiconductor layer 1. In addition, the porosity can be changed by controlling the molecular weight or addition amount of the organic compound that is burned during calcination.

As the organic compound to be used, any of organic compounds that are dissolved in the suspension and removed by burning during calcination can be used. Examples of the organic compound include polymers or copolymers of the vinyl compounds of polyethylene glycol, cellulose ester resins, cellulose ether resins, epoxy resins, urethane resins, phenol resins, polycarbonate resins, polyarylate resins, polyvinyl butyral resins, polyester resins, polyvinyl formal resins, silicone resins, styrenes, vinyl acetate, acrylic acid esters, methacrylic acid esters, or the like. The kind or amount of the resin can be appropriately selected and adjusted depending on the state of fine particles to be used, the total weight of the entire suspension, or the like. However, if the proportion of the semiconductor fine particles is more than or equal to 10% by weight relative to the total weight of the entire suspension, the strength of the film prepared can be more sufficiently enhanced, and if the proportion of the semiconductor fine particles is less than or equal to 40% by weight relative to the total weight of the entire suspension, a porous semiconductor layer 1 having a high porosity can be obtained more stably, and therefore, the proportion of the semiconductor fine particles is preferably more than or equal to 10% by weight and less than or equal to 40% by weight, relative to the total weight of the entire suspension.

As the semiconductor fine particles, particles or the like of singular or plural compound semiconductors having a suitable average particle diameter, for example, an average particle diameter of more than or equal to about 1 nm and less than or equal to 500 nm, are preferably used. Among these, the average particle diameter is preferably more than or equal to about 1 nm and less than or equal to about 50 nm, from the viewpoint of increasing the specific surface area. In addition, a semiconductor particle having a relatively large average particle diameter of more than or equal to about 200 nm and less than or equal to about 400 nm may be added in order to increase the utilization of the incident light.

In addition, examples of the method for preparing the semiconductor fine particles include a sol-gel method such as a hydrothermal synthesis method; a sulfuric acid method; and a chlorine method. Any of the methods capable of preparing desired fine particles may be used, however, from the viewpoint of crystallinity, the semiconductor fine particles are preferably synthesized by a hydrothermal synthesis method.

Examples of the dispersion medium of the suspension include glyme-based solvents such as ethylene glycol monomethyl ether; alcohols such as isopropyl alcohol; a mixed solvent of isopropyl alcohol/toluene; and water.

Examples of the method of coating the suspension include known methods such as a doctor blade method, a squeegee method, a spin coating method, and a screen printing method. Further, after coating the suspension, the coating film is dried and calcined. As for the conditions for drying and calcining, the drying and calcining are carried out, for example, at a temperature in the range of about 50° C. to 800° C. for approximately 10 seconds to 12 hours under air or under an inert gas atmosphere. This drying and calcining can be carried out once at a single temperature, or twice or more at varying temperatures.

Furthermore, the method for forming a porous semiconductor layer 1 has been described in detail above, and other types of semiconductor layer 1 may also be formed using various known methods.

<Dye>

For the dye in the photoelectric conversion element of the present embodiment, the maleimide-based compound of the present embodiment represented by the general formula (1) as described above is used.

Examples of the method for adsorbing the dye on the semiconductor layer 1 include a method in which a semiconductor substrate, a conductive substrate including the semiconductor layer 1 is immersed in a solution having a dye dissolved therein, and a method in which a dye solution is coated on a semiconductor layer 1 and adsorbed thereon.

Examples of the solvent for the solution include nitrile-based solvents such as acetonitrile, propionitrile, and methoxyacetonitrile, alcohol-based solvents such as methanol, ethanol, and isopropyl alcohol, ketone-based solvents such as acetone, methyl ethyl ketone, methyl isobutyl ketone, and cyclohexanone, ester-based solvents such as ethyl acetate and butyl acetate, ether-based solvents such as tetrahydrofuran and dioxane, amide-based solvents such as N,N-dimethylformamide, N,N-dimethylacetamide, and N-methyl-2-pyrrolidone, halogen-based solvents such as dichloromethane, chloroform, dichloroethane, trichloroethane, and chlorobenzene, hydrocarbon-based solvents such as toluene, xylene, and cyclohexane, and water. These may be used alone or in combination of two or more kinds thereof.

Further, when immersed in the dye solution for a certain period of time, the solution can be stirred or heated to reflux; or an ultrasonic wave can also be applied thereto. In addition, after adsorbing the dye, in order to remove the remaining dye which was not adsorbed, it is desirable to wash with a solvent such as an alcohol.

The amount of the dye to be carried is in the range of $1\times10^{-10}$ mol/cm$^2$ to $1\times10^{-4}$ mol/cm$^2$, and particularly preferably in the range of $1\times10^{-9}$ mol/cm$^2$ to $9.0\times10^{-6}$ mol/cm$^2$. Within these ranges, it is possible to obtain an effect of economically and sufficiently improving the photoelectric conversion efficiency.

Moreover, in order to increase the conversion efficiency as well as to widen the wavelength band capable of performing photoelectric conversion as large as possible, the dye can be used in a mixture of two or more kinds thereof, and in this case, it is preferable to select the kind and the ratio of the dye appropriately in consideration of the absorption wavelength band and the strength of the dye.

In addition, in order to suppress a decrease in the conversion efficiency due to association between the dyes, additives may be used in combination when the dye is adsorbed. Examples of the additive include steroidal compounds having a carboxy group (for example, deoxycholic acid, cholic acid, and chenodeoxycholic acid).

<Counter Electrode>

The counter electrode 8 in the present embodiment has a catalyst layer 6 on a substrate 7. In the photoelectric conversion element of the present embodiment, holes generated from the dye adsorbed on the semiconductor layer 1 due to the incident light are transferred to the counter electrode 8 through the electrolyte layer 5, however, the counter electrode 8 is not particularly limited in the materials therefor as long as it can complete its function of efficient pair annihilation of electrons and holes. The catalyst layer 6 of the counter electrode 8 may be made into a metal-deposited film formed on a substrate 7 by a vapor deposition method or the like. For example, the catalyst layer may be a Pt layer formed on the substrate 7. In addition, the catalyst layer 6 of the counter electrode 8 may include a nano-carbon material. For example, the catalyst layer 6 of the counter electrode 8 can be formed by sintering a paste containing carbon nanotubes, carbon nanohorns, or carbon fibers on a porous insulating film. The nano-carbon materials have a large specific surface area and can improve the probability of pair annihilation of electrons and holes. Examples of the substrate 7 include transparent substrates such as glass and a polymer film, and metal plates (foil). In addition, in order to prepare the counter electrode 8 of the light transmission, the counter electrode 8 can be prepared by selecting glass with a transparent conductive film as the substrate 7, and forming platinum, carbon, or the like as the catalyst layer 6, using a vapor deposition method or a sputtering method.

<Electrolyte Layer>

The electrolyte layer 5 used in the present embodiment is required to have a function to transport holes generated from the dye adsorbed on the semiconductor layer 1 due to the incident light to the counter electrode 8, and an electrolytic liquid having redox pairs dissolved in an organic solvent, a gel electrolyte in which a liquid having redox pairs dissolved in an organic solvent is impregnated in a polymer matrix, a molten salt containing a redox pair, a solid electrolyte, an organic hole transport material, or the like can be used. Further, the electrolyte layer 5 is constituted with an electrolyte, a solvent, and additives.

Examples of the electrolyte include combinations of iodides including metal iodides such as LiI, NaI, KI, CsI, and CaI$_2$, and iodine salts of quaternary ammonium compounds such as tetraalkylammonium iodide, pyridinium iodide, and imidazolium iodide with I$_2$; combinations of bromides including metal bromides such as LiBr, NaBr, KBr, CsBr, and CaBr$_2$, and bromine salts of quaternary ammonium compounds such as tetraalkylammonium bromide and pyridinium bromide with Br$_2$; metal complexes such as a ferrocyanide salt-ferricyanide salt, and ferrocene-ferrocenium ions; sulfur compounds such as sodium polysulfide and alkyl thiol-alkyl disulfide; viologen dyes; and hydroquinone-quinone. Among these, combinations of LiI, pyridinium iodide, or imidazolium iodide with I$_2$ are preferred. Further, the electrolytes may be used alone or in a mixture of two or more kinds thereof. Further, as the electrolyte, a molten salt in the molten state at room temperature can be used as the electrolyte, and in this case, particularly, a solvent may not be used.

Examples of the solvent of the electrolyte layer 5 include carbonate-based solvents such as ethylene carbonate, diethyl carbonate, dimethyl carbonate, and propylene carbonate, amide-based solvents such as N-methyl-2-pyrrolidone and N,N-dimethylformamide, nitrile-based solvents such as methoxypropionitrile, propionitrile, methoxy acetonitrile, and acetonitrile, lactone-based solvents such as γ-butyrolactone and valerolactone, ether-based solvents such as tetrahydrofuran, dioxane, diethyl ether, and ethylene glycol dialkyl ether, alcohol-based solvents such as methanol, ethanol, and isopropyl alcohol, aprotic polar solvents such as dimethyl sulfoxide and sulfolane, and heterocyclic compounds such as 2-methyl-3-oxazolidinone and 2-methyl-1,3-dioxolane. These solvents may be used in a mixture of two or more kinds thereof, if desired.

Furthermore, basic additives may be added to the electrolyte layer 5 in the present embodiment in order to suppress dark current. The kind of the basic additive is not particularly limited, and examples thereof include t-butylpyridine, 2-picoline, and 2,6-lutidine. In the case of adding the basic compound, the addition concentration is more than or equal to about 0.05 mol/L and less than or equal to 2 mol/L.

Furthermore, as the electrolyte, a solid electrolyte can be used. In this case, as the solid electrolyte, a complete solid electrolyte or a gel electrolyte can be used.

As a gel electrolyte, those obtained by adding electrolytes or molten salts at room temperature into a gelling agent can be used. As for the gelling method, gelling can also be carried out by a method such as addition of an oil gelling agent or a polymer, polymerization of coexisting polyfunctional monomers, and a crosslinking reaction of polymers. Examples of the polymers when gelling is carried out by the addition of the polymer include polyacrylonitrile and polyvinylidene fluoride. Further, examples of the oil gelling agent include dibenzylidene-D-sorbitol, cholesterol derivatives, amino acid derivatives, alkyl amide derivatives of trans-(1R,2R)-1,2-cyclohexanediamine, alkyl urea derivatives, N-octyl-D-gluconamide benzoate, double-headed amino acid derivatives, quaternary ammonium salt derivatives.

In the case of polymerization with polyfunctional monomers, the monomer to be used is preferably a compound having two or more ethylenically unsaturated groups, and examples thereof include divinylbenzene, ethylene glycol dimethacrylate, ethylene glycol diacrylate, diethylene glycol dimethacrylate, diethylene glycol diacrylate, triethylene glycol dimethacrylate, triethylene glycol diacrylate, pentaerythritol triacrylate, and trimethylolpropane triacrylate.

Moreover, monofunctional monomer other than the above-described polyfunctional monomers may also be added. Examples of the monofunctional monomers include esters or amides derived from acrylic acids or α-alkylacrylic acids, such as acrylamide, N-isopropylacrylamide, methylacrylate, and hydroxyethyl acrylate, esters derived from maleic acid or fumaric acid, such as dimethyl maleate, diethyl fumarate, and dibutyl maleate, dienes such as butadiene, isoprene, and cyclopentadiene, aromatic vinyl compounds such as styrene, p-chlorostyrene, and sodium styrene sulfonate, vinyl esters such as vinyl acetate, nitriles such as acrylonitrile and methacrylonitrile, vinyl compounds having nitrogen-containing heterocyclic rings such as vinyl carbazole, vinyl compounds having quaternary ammonium salts, N-vinylformamide, vinylsulfonic acid, vinylidene fluoride, vinyl alkyl ethers, and N-phenylmaleimide. The amount of the polyfunctional monomers occupied by the total amount of the monomers is preferably from more than or equal to 0.5% by mass and less than or equal to 70% by mass, and more preferably more than or equal to 1.0% by mass and less than or equal to 50% by mass.

The above-described monomers can be polymerized by a radical polymerization method. The radical polymerization of the monomers for a gel electrolyte can be carried out by heating, light, ultraviolet rays, or electron beam, or electrochemically. Examples of the polymerization initiator used in the case of forming a crosslinked polymer by heating include azo-based initiators such as 2,2'-azobis(isobutyronitrile) and 2,2'-azobis(dimethylvaleronitrile), and peroxide-based initiators such as benzoyl peroxide. The addition amount of the polymerization initiator is preferably more than or equal to 0.01% by mass and less than or equal to 15% by mass, and more preferably more than or equal to 0.05% by mass and less than or equal to 10% by mass, relative to the total amount of the monomers.

If the electrolyte is gelled by the crosslinking reaction of polymers, it is preferable to use a combination of a polymer containing reactive groups required for the crosslinking reaction, and a crosslinking agent. The preferred crosslinkable reactive group is a nitrogen-containing heterocyclic ring such as a pyridine ring, an imidazole ring, a triazole ring, an oxazole ring, a triazole ring, a morpholine ring, a piperidine ring, and a piperazine ring, and the preferred crosslinking agent is a bifunctional or higher reagent capable of performing an electrophilic substitution reaction with a nitrogen atom, such as alkyl halide, aralkyl halide, sulfonic acid ester, acid anhydride, acid chloride, and isocyanate.

Furthermore, as the complete solid electrolyte, a mixture of an electrolyte and an ion conductive polymer compound can be used. Examples of the ion conductive polymer compound include polar polymer compounds such as polyethers, polyesters, polyamines, and polysulfides.

Moreover, when an inorganic solid electrolyte is used as the electrolyte, copper iodide, copper thiocyanate, or the like can be introduced into the electrode by a method such as a cast method, a coating method, a spin coating method, a dipping method, and an electroplating method.

Furthermore, in the present embodiment, an organic hole transport material can be used instead of the electrolyte. Examples of the organic hole transport material include aromatic diamines such as 2,2',7,7'-tetrakis(N,N-di-p-methoxyphenyl amine)-9,9'-spirobifluorene (Adv. Mater. 2005, 17, 813) and N,N'-diphenyl-N,N'-bis(3-methylphenyl)-(1,1'-biphenyl)-4,4'-diamine (U.S. Pat. No. 4,764,625); triphenylamine derivatives (Japanese Laid-open Patent Publication No. H04-129271); stilbene derivatives (Japanese Laid-open Patent Publication No. H02-51162); and hydrazone derivatives (Japanese Laid-open Patent Publication No. H02-226160).

Moreover, the organic hole transport material can be introduced into the electrode by, for example, a vacuum deposition method, a casting method, a spin coating method, a dipping method, and an electrolytic polymerization method.

As a method for preparing the electrolyte layer 5 of the present embodiment, there are two methods at large, that is, a method in which the counter electrode 8 is adhered in advance on the semiconductor layer 1 having a dye adsorbed thereon, and the liquid electrolyte layer 5 is sandwiched into the gap therebetween, and a method in which the electrolyte layer 5 is directly formed on the semiconductor layer 1. In the latter case, the electrolyte layer 5 is formed, and then, the counter electrode 8 is formed thereon.

The above-described photoelectric conversion element of the present embodiment can be used in, for example, a solar cell. Further, the means therefor can be attained in accordance with prior art, and thus, will not be referenced in the described description herein.

EXAMPLES

Hereinbelow, the present invention will be described in more detail with reference to Examples.

Example 1

Synthesis of Maleimide-Based Compound M1

[Chem. 11]

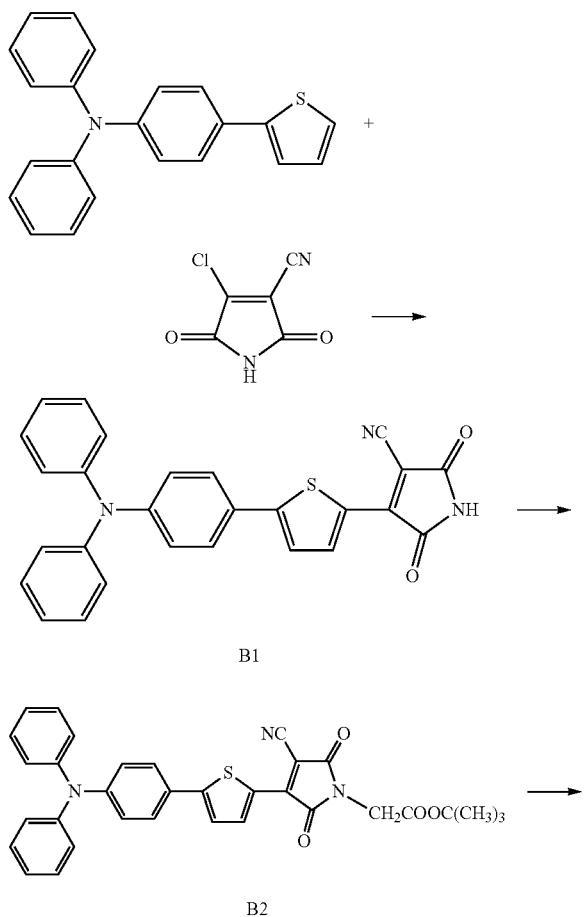

B1

B2

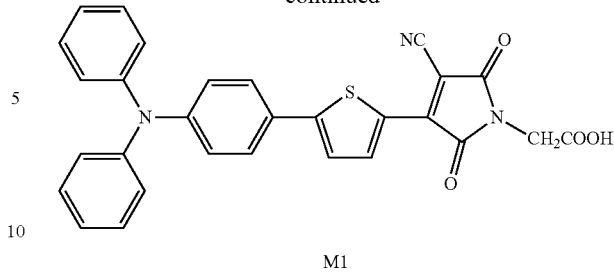

M1

2 g of 2-chloro-3-cyanomaleimide (synthesized by the method described in J. Am. Chem. Soc., 80, p. 1385-1388 (1958)) was dissolved in 100 ml of acetonitrile, and 4.19 g of 4-(thiophen-2-yl)triphenylamine was added thereto, followed by allowing them to undergo a reaction at room temperature overnight. The reaction mixture was washed with 600 ml of water, and the precipitated crystal was separated by filtration and washed several times with warm water. In addition, the resultant was washed with 100 ml of ethanol under heating and stirring to obtain 3.15 g (yield 55%) of a compound B1.

Next, 2 g of the compound B1 and 1.31 g of t-butyl bromoacetate were dissolved in 80 ml of acetonitrile, and 0.62 g of potassium carbonate was added thereto, followed by stirring at 80° C. for 2 hours. Further, after leaving to cool, 1000 ml of ice water was poured thereinto and the precipitated crystal was separated by filtration. In addition, the crystal was washed with 110 ml of hexane/ethyl acetate (10/1) under heating and stirring, and then separated by filtration to obtain 1.20 g (yield 48%) of a compound B2.

Next, 1 g of the compound B2 and 0.406 g of p-toluenesulfonic monohydrate were dissolved in 40 ml of acetonitrile, followed by heating and refluxing for 1 hour. After leaving to be cooled, 400 ml of ice water was poured thereinto and the precipitated crystal was separated by filtration and washed with water. In addition, the crystal was washed several times with warm water to obtain 0.39 g (yield 44%) of a desired maleimide-based compound M1.

Furthermore, the $\lambda_{max}$ of the obtained dye in acetonitrile was 563 nm.

Example 2

Synthesis of Maleimide-Based Compound M2

[Chem. 12]

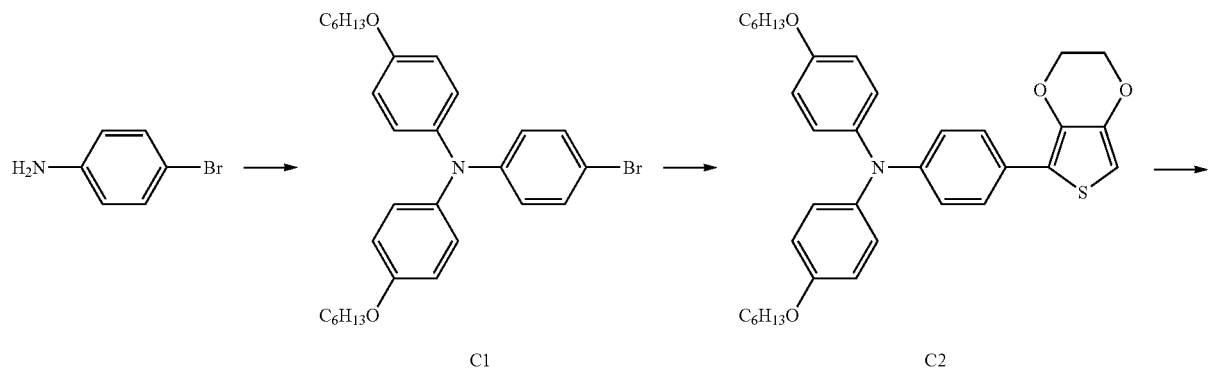

C1

C2

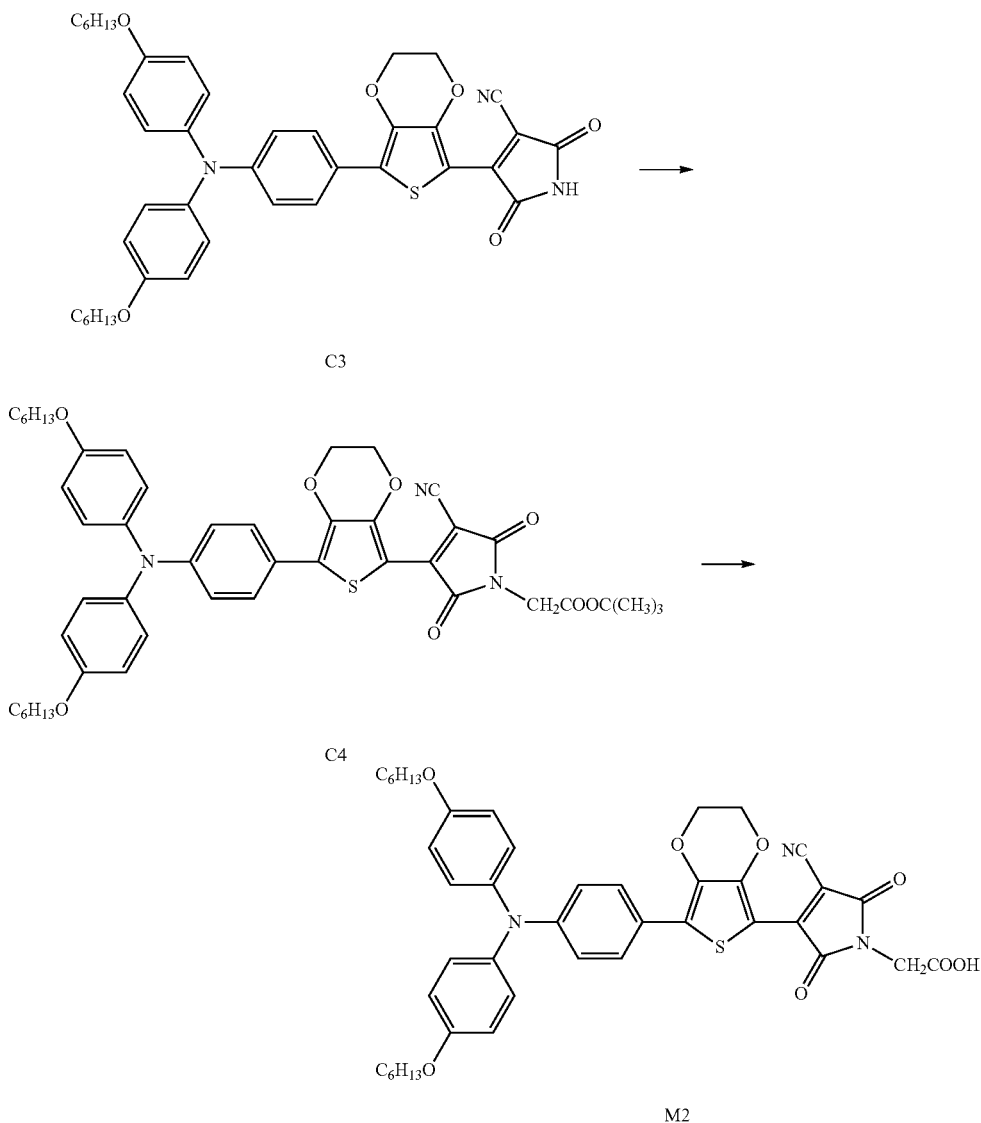

A solution of 7.16 g of p-bromoaniline, 32 g of p-hexyloxyiodobenzene, and 1.51 g of 1,10-phenanthroline in toluene (84 ml) was heated to 100° C., and 20.75 g of potassium hydroxide and 0.831 g of copper (I) chloride were added thereto, followed by stirring for 24 hours. After leaving to cool, the resultant was separated by filtration and washed with toluene, and the solvent was evaporated under reduced pressure. The residue was separated and purified by silica gel columns (eluent: hexane/chloroform=5/1) to obtain 10.9 g of a compound C1.

Next, 3.6 g of tetrakis(triphenylphosphinepalladium) was added to a solution of 163.6 g of the compound C1 and 173 g of 2-tributyltin-3,4-ethylenedioxythiophene in 2400 ml of anhydrous toluene, followed by heating and refluxing for 40 hours. The solvent was evaporated under reduced pressure, and separated and purified by silica gel columns (eluent: hexane/toluene=1/1) to obtain 75.19 g of a compound C2.

Next, 2.19 g of the compound C2 was dissolved in 150 ml of acetonitrile, and 0.5852 g of 2-chloro-3-cyanomaleimide was added thereto, followed by stirring at room temperature for 20 hours. The precipitated crystal was separated by filtration and washed with acetonitrile to obtain 2.45 g of a compound C3.

Next, 0.7 g of the compound C3 and 0.291 g of t-butyl bromoacetate were dissolved in 30 ml of dioxane, and 0.137 g of potassium carbonate was added thereto, followed by stirring at 80° C. for 4 hours. Further, after leaving to be cooled, 500 ml of water was poured thereinto and the precipitated crystal was separated by filtration. In addition, the crystal was dissolved in tetrahydrofuran (THF), and reprecipitated in hexane to obtain 0.71 g of a compound C4.

Next, 0.3 g of the compound C4 and 0.104 g of p-toluenesulfonic monohydrate were dissolved in 40 ml of toluene, followed by stirring at 80° C. for 6 hours. After leaving to be cooled, the resultant was concentrated under reduced pressure, and the residue was dissolved in tetrahydrofuran (THF), and reprecipitated in hexane to obtain 0.212 g of a desired maleimide-based compound M2 (yield 76%).

Furthermore, the $\lambda_{max}$ of the obtained dye in acetonitrile was 618 nm.

Example 3
Synthesis of Maleimide-Based Compound M3
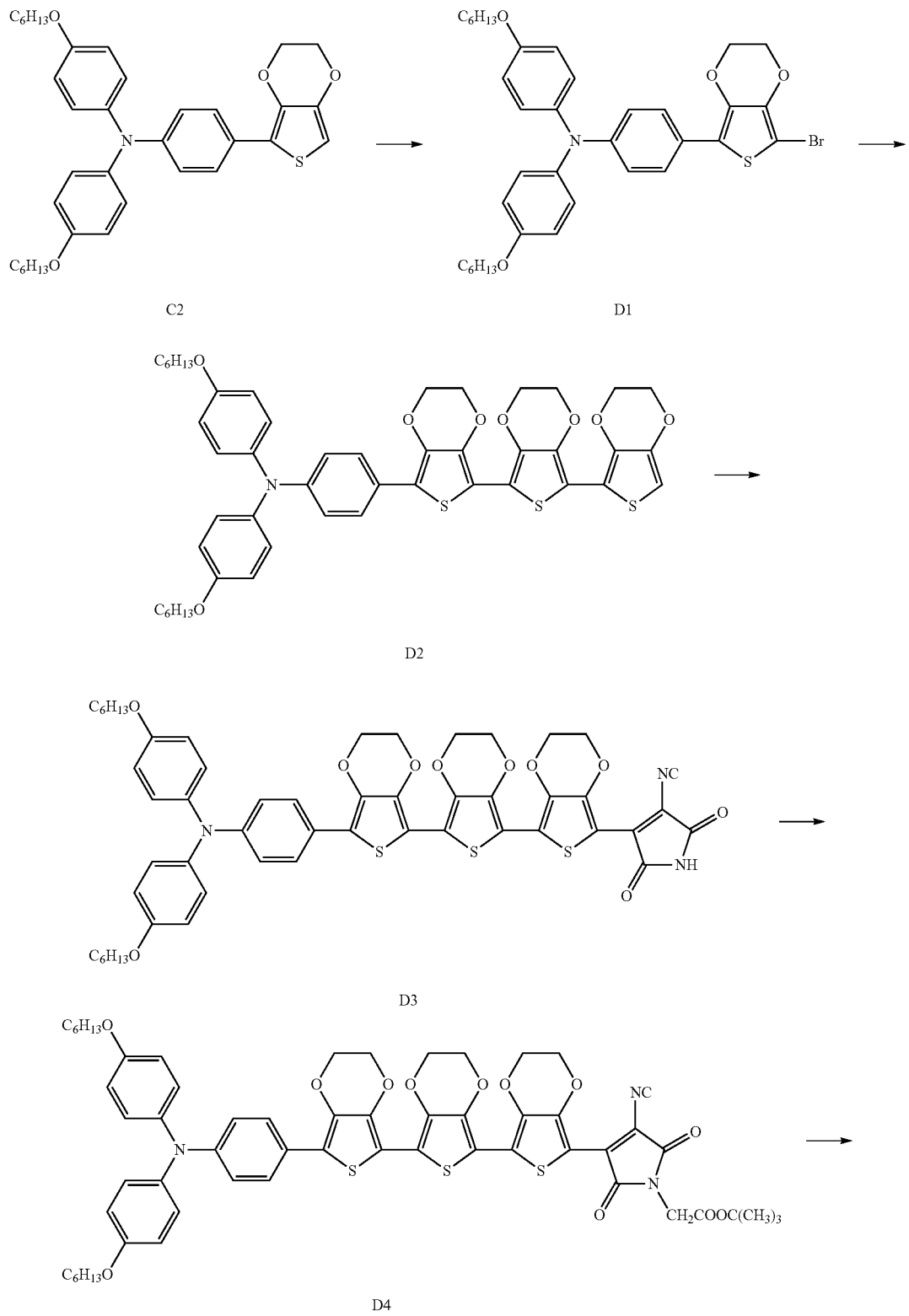

-continued

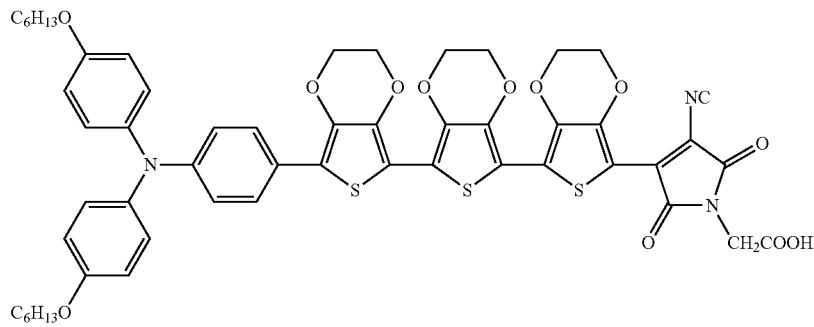

M3

4.8 g of the compound C2 was dissolved in 60 ml of N,N-dimethylformamide (DMF), and a solution having 1.6 g of N-bromosuccinimide dissolved in 10 ml of DMF was added dropwise thereto under ice-cooling. Thereafter, after stirring for 4 hours, water was added to the reaction mixture, and the organic layer was extracted with ethyl acetate. After drying over magnesium sulfate, the solvent was evaporated under reduced pressure, and the residue was separated and purified by silica gel columns (eluent: hexane/ethyl acetate=5/1) to obtain 3.929 g of a compound D1.

Next, 0.11 g of tetrakis(triphenylphosphinepalladium) was added to a solution of 2 g of the compound D1 and 2.235 g of 5-tributyltin-2,2'-bis(3,4-ethylenedioxythiophene) in 30 ml of anhydrous toluene, followed by heating and refluxing for 12 hours. The solvent was evaporated under reduced pressure, and the residue was washed with 80 ml of hot methanol three times to obtain 1.647 g of a compound D2.

Next, 0.63 g of the compound D2 was dissolved in 400 ml of acetonitrile, and 0.114 g of 2-chloro-3-cyanomaleimide was added thereto, followed by stirring at room temperature for 12 hours. The reaction solution was evaporated under reduced pressure, and the residue was dissolved in THF and reprecipitated in methanol to obtain 0.51 g of a compound D3.

Next, 0.4 g of the compound D3 and 0.119 g of t-butyl bromoacetate were dissolved in 30 ml of dioxane, and 0.056 g of potassium carbonate was added thereto, followed by stirring at 80° C. for 4 hours. Further, after leaving to be cooled, the resultant was poured into 500 ml of water, and the precipitated crystal was separated by filtration. In addition, the crystal was dissolved in tetrahydrofuran (THF) and reprecipitated in hexane to obtain 0.33 g of a compound D4.

Next, 0.3 g of the compound C4 and 0.078 g of p-toluenesulfonic monohydrate were dissolved in 40 ml of toluene, followed by stirring at 80° C. for 6 hours. After leaving to be cooled, the resultant was concentrated under reduced pressure, and the residue was dissolved in tetrahydrofuran (THF) and reprecipitated in 400 ml of water to obtain 0.168 g (yield 59%) of a desired maleimide-based compound M3.

Furthermore, the $\lambda_{max}$ of the obtained dye in tetrahydrofuran was 665 nm.

Example 4

Synthesis of Maleimide-Based Compound M4

[Chem. 14]

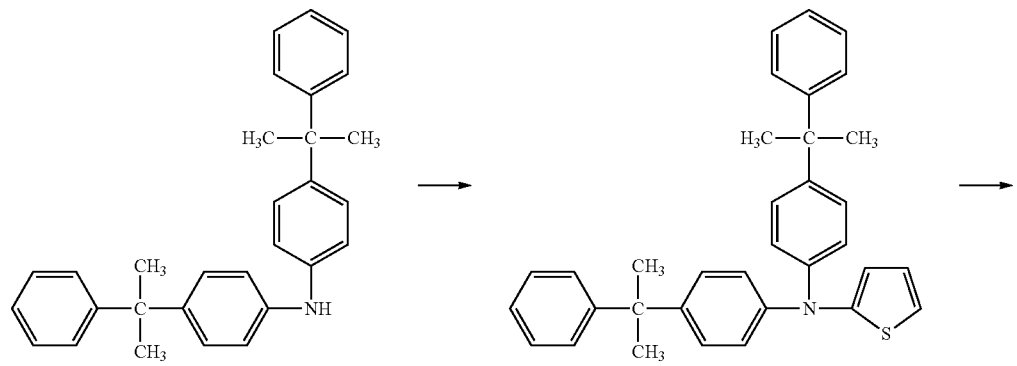

E1

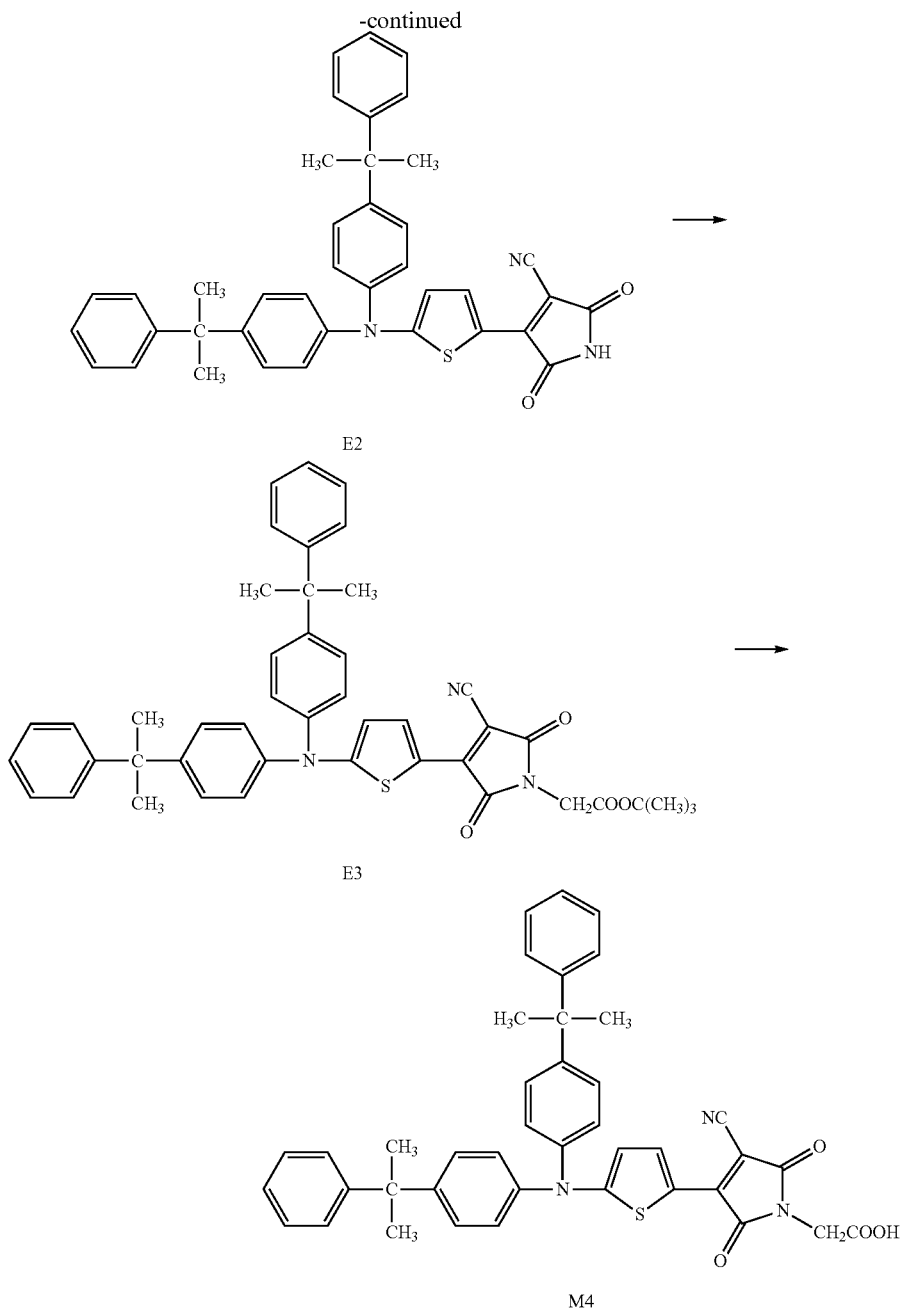

48.1 g of 2-bromothiophene and 80 g of 4,4'-bis(α,α-dimethylbenzyl)diphenylamine were dissolved in 390 ml of toluene, and 28.4 g of sodium t-butoxide, 1.59 g of tri-t-butylphosphine, and 0.441 g of palladium (II) acetate were added thereto, followed by refluxing for 2 hours. After cooling to room temperature and washing with water, the organic layer was dried over magnesium sulfate. The solvent was evaporated under reduced pressure, and the residue was separated and purified by silica gel columns (eluent: hexane/toluene=9/1) to obtain 43.3 g of a compound E1.

Next, 2 g of the compound E1 was dissolved in 100 ml of acetonitrile, and 0.642 g of 2-chloro-3-cyanomaleimide was added thereto, followed by stirring at room temperature for 4 hours. The reaction solution was evaporated under reduced pressure and the residue was dissolved in THF and reprecipitated in 400 ml of water to obtain 2.511 g of the compound E2.

Next, 0.5 g of the compound E2 and 0.241 g of t-butyl bromoacetate were dissolved in 30 ml of acetonitrile, and 0.114 g of potassium carbonate was added thereto, followed by stirring at 80° C. for 2 hours. Further, after leaving to cool, the resultant was poured into 400 ml of water, and the precipitated crystal was separated by filtration. In addition, the crystal was dissolved in tetrahydrofuran (THF) and reprecipitated in hexane to obtain 0.399 g of a compound E3.

Next, 0.3 g of the compound E3 and 0.119 g of p-toluenesulfonic monohydrate were dissolved in 40 ml of toluene, followed by stirring at 80° C. for 4 hours. After leaving to cool, the resultant was concentrated under reduced pressure and the residue was dissolved in tetrahydrofuran (THF) and reprecipitated in 400 ml of water to obtain 0.147 g (yield 53%) of a desired maleimide-based compound M4.

Furthermore, the $\lambda_{max}$ of the obtained dye in acetonitrile was 575 nm.

Example 5

Preparation of Photoelectric Conversion Element

<<Preparation of Semiconductor Electrode and Counter Electrode>>

First, the semiconductor electrode was prepared in the following order. FTO-coated glass (10 Ωcm²) in 15 mm×15 mm, having a thickness of 1.1 mm, was prepared as a conductive substrate (light-transmissive substrate with a transparent conductive layer).

Next, a titanium oxide paste to be a material for a semiconductor layer was prepared by stirring 5 g of commercially available titanium oxide powder (trade name: P25, manufactured by Nippon Aerosil Co., Ltd.), 20 ml of a 15%-by-volume aqueous acetic acid solution, 0.1 ml of a surfactant (trade name: Triton (registered trademark) X-100, manufactured by Sigma-Aldrich Corporation), and 0.3 g of polyethylene glycol (molecular weight 20000) (manufactured by Wako Pure Chemical Industries, Ltd., product code 168-11285) with a stirring mixer for about 1 hour.

Next, the titanium oxide paste was coated in an appropriate amount onto FTO-coated glass by a doctor blade method to give a film thickness of about 50 μm (coating area: 10 mm×10 mm). Thereafter, the FTO-coated glass on which the titanium oxide paste had been coated was inserted into an electric surface, calcined at 450° C. for about 30 minutes under an air atmosphere, and naturally cooled to form a porous titanium oxide semiconductor layer as a semiconductor layer.

Moreover, in order to form a light scattering layer, titanium oxide having an average particle diameter of 300 nm was mixed with the above-described titanium oxide paste at a weight ratio of 20% relative to the titanium oxide paste to prepare a paste. Further, the paste was coated on the above-described porous titanium oxide semiconductor layer to a thickness of 20 μm by a screen printing method, then calcined at 450° C. for about 30 minutes under an air atmosphere, and naturally cooled.

Furthermore, a platinum layer at an average film thickness of 1 μm as a catalyst layer was deposited on a soda lime glass plate (thickness of 1.1 mm) by a vacuum deposition method as a counter electrode for the preparation.

<<Dye Adsorption>>

Next, the dye was adsorbed on the surface of a semiconductor layer made of the above-described thin titanium oxide film. For the dye, a solution formed by dissolving the maleimide-based compound M1 synthesized in Example 1 in acetonitrile at a concentration of about 2×10⁻⁴ M was used. The semiconductor electrode having the above-described porous titanium oxide semiconductor layer was immersed in the dye solution, and stored overnight. Thereafter, the semiconductor electrode was taken out from the dye solution and rinsed with acetonitrile, and the excess dye was removed and then dried in air.

<<Cell Assembly>>

The above-described semiconductor electrode after the dye adsorption treatment and the above-described counter electrode were disposed to make the semiconductor layer and the catalyst layer face each other, and the periphery of the cell portion was thermally compressed by a thermosetting resin film having a cut surface sufficient for the electrolyte layer to penetrate into the gap.

<<Injection of Electrolyte Layer>>

An iodine-based electrolyte as an electrolyte layer was injected into the above-described cell from the counter electrode side using surface tension. The iodine-based electrolyte was prepared using acetonitrile as a solvent, and adjusting the concentrations of the respective components to 0.5 mol/L of iodine, 0.1 mol/L of lithium iodide, 0.5 mol/L of 4-tert-butylpyridine, and 0.6 mol/L of 1,2-dimethyl-3-propylimidazolium iodide.

<<Measurement of Photocurrent>>

The photoelectric conversion element as prepared above was irradiated with light at an intensity of 100 mW/cm² under the condition of AM 1.5 with a solar simulator. The generated electricity was measured by a current-voltage measurement device and the photoelectric conversion characteristics were evaluated, and as a result, a photoelectric conversion efficiency of 3.4% could be obtained.

Example 6

In the same manner as in Example 5 except that a maleimide-based compound M2 was used instead of the maleimide-based compound M1, a photoelectric conversion element was prepared. The photoelectric conversion characteristics of the obtained photoelectric conversion element were evaluated, and as a result, a photoelectric conversion efficiency of 2.5% could be obtained with the element using M2.

Example 7

In the same manner as in Example 5 except that a maleimide-based compound M3 was used instead of the maleimide-based compound M1, a photoelectric conversion element was prepared. The photoelectric conversion characteristics of the obtained photoelectric conversion element were evaluated, and as a result, a photoelectric conversion efficiency of 4.2% could be obtained with the element using M3.

Example 8

In the same manner as in Example 5 except that a maleimide-based compound M4 was used instead of the maleimide-based compound M1, a photoelectric conversion element was prepared. The photoelectric conversion characteristics of the obtained photoelectric conversion element were evaluated, and as a result, a photoelectric conversion efficiency of 4.6% could be obtained with the element using M4.

As clearly seen from the above description, by using the maleimide-based compound of the present invention for a dye for photoelectric conversion, excellent photoelectric conversion efficiency can be obtained. The photoelectric conversion dye of the present invention can be used for a semiconductor electrode, a photoelectric conversion element, a solar cell, or the like.

The present application claims priority on the basis of Japanese Patent Application No. 2010-114568 filed on May 18, 2010, the disclosure of which is hereby incorporated by reference in its entirety.

The invention claimed is:

1. A maleimide-based compound represented by the following general formula (1), and a tautomer or a stereoisomer thereof:

[Chem. 1]

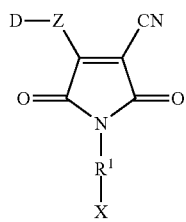

(1)

wherein in the formula (1), $R^1$ represents a direct bond, or a substituted or unsubstituted alkylene group, X represents an acidic group, D represents an organic group containing an electron-donating substituent, Z represents a linking group that has at least one hydrocarbon group selected from aromatic rings or heterocyclic rings.

2. The maleimide-based compound, and the tautomer or the stereoisomer thereof according to claim 1, wherein the acidic group is a carboxyl group, a sulfonic acid group, or a phosphonic acid group.

3. The maleimide-based compound, and the tautomer or the stereoisomer thereof according to claim 1, wherein the organic group containing an electron-donating substituent is an organic group having a structure represented by the following general formula (2) or (3):

[Chem. 2]

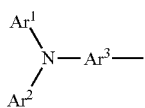

(2)

[Chem. 3]

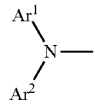

(3)

wherein $Ar^1$ and $Ar^2$ in the formula (2) each independently represent a substituted or unsubstituted alkyl group, a substituted or unsubstituted aryl group, or a heterocyclic group, $Ar^3$ represents a substituted or unsubstituted arylene group, or a substituted or unsubstituted divalent heterocyclic group.

4. The maleimide-based compound, and the tautomer or the stereoisomer thereof according to claim 1, wherein the linking group Z is a linking group having at least a structure represented by the following general formula (4):

[Chem. 4]

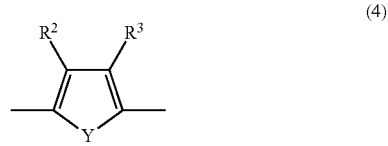

(4)

in the general formula (4), $R^2$ and $R^3$ each independently represent a hydrogen atom, a substituted or unsubstituted alkyl or alkoxy group, or $R^2$ and $R^3$ may be bonded to each other to form a ring, Further, Y represents an oxygen atom, a sulfur atom, or NRa, and Ra represents a hydrogen atom, a substituted or unsubstituted alkyl group, or a substituted or unsubstituted aryl group.

5. A dye for photoelectric conversion, comprising at least one of the maleimide-based compound, and the tautomer or the stereoisomer thereof according to claim 1.

6. A semiconductor electrode comprising a semiconductor layer having the dye for photoelectric conversion according to claim 5.

7. The semiconductor electrode according to claim 6, wherein the semiconductor layer contains titanium oxide or zinc oxide.

8. A photoelectric conversion element comprising the semiconductor electrode according to claim 6.

9. A photoelectrochemical cell comprising the photoelectric conversion element according to claim 8.

* * * * *

UNITED STATES PATENT AND TRADEMARK OFFICE
CERTIFICATE OF CORRECTION

PATENT NO. : 8,933,329 B2
APPLICATION NO. : 13/697974
DATED : January 13, 2015
INVENTOR(S) : Katsumi Maeda, Shin Nakamura and Kentaro Nakahara Page 1 of 1

It is certified that error appears in the above-identified patent and that said Letters Patent is hereby corrected as shown below:

In the claims

Column 36, Line 26: In Claim 4, delete "ring, Further," and insert -- ring, --

Signed and Sealed this
Fifth Day of January, 2016

Michelle K. Lee
*Director of the United States Patent and Trademark Office*